United States Patent [19]
Littleton et al.

[11] Patent Number: 5,792,531
[45] Date of Patent: Aug. 11, 1998

[54] READILY DONNED, POWDER FREE ELASTOMERIC ARTICLE

[75] Inventors: Kermit R. Littleton, Julian; Garth Brown, Alpine; Sebastian Plamthottam, Upland, all of Calif.

[73] Assignee: Tactyl Technologies, Inc., Vista, Calif.

[21] Appl. No.: 604,009

[22] Filed: Feb. 20, 1996

[51] Int. Cl.⁶ ............................................... B32B 1/08
[52] U.S. Cl. .................... 428/36.8; 428/516; 428/517; 428/519; 428/521; 428/522; 2/161.7; 2/168
[58] Field of Search ............... 2/161.7, 168; 428/36.8, 428/517, 516, 519, 521, 522

[56] References Cited

U.S. PATENT DOCUMENTS 5,451,439  9/1995  Bigg ........................................ 428/36.8

*Primary Examiner*—Charles Nold
*Attorney, Agent, or Firm*—Gregory Garmong

[57] ABSTRACT

An elastomeric article such as a glove includes a substrate body made of an styrene-ethylene-butylene-styrene block copolymer, and a donning layer overlying at least one side of the substrate body. The donning layer is formed of a chlorinated styrene-isoprene, preferably having a polystyrene block content of from about 10 to about 20 percent by weight of the total copolymer weight and an end block polystyrene molecular weight of at least about 5,000. Optionally, a surfactant-containing layer may be present over the donning layer to further improve the donning characteristics. The article is preferably prepared by dip forming the article from an styrene-ethylene-butylene-styrene block copolymer, coating the article with a solution of the styrene-isoprene block copolymer, removing the solvent, and chlorinating the styrene-isoprene block copolymer.

20 Claims, 3 Drawing Sheets

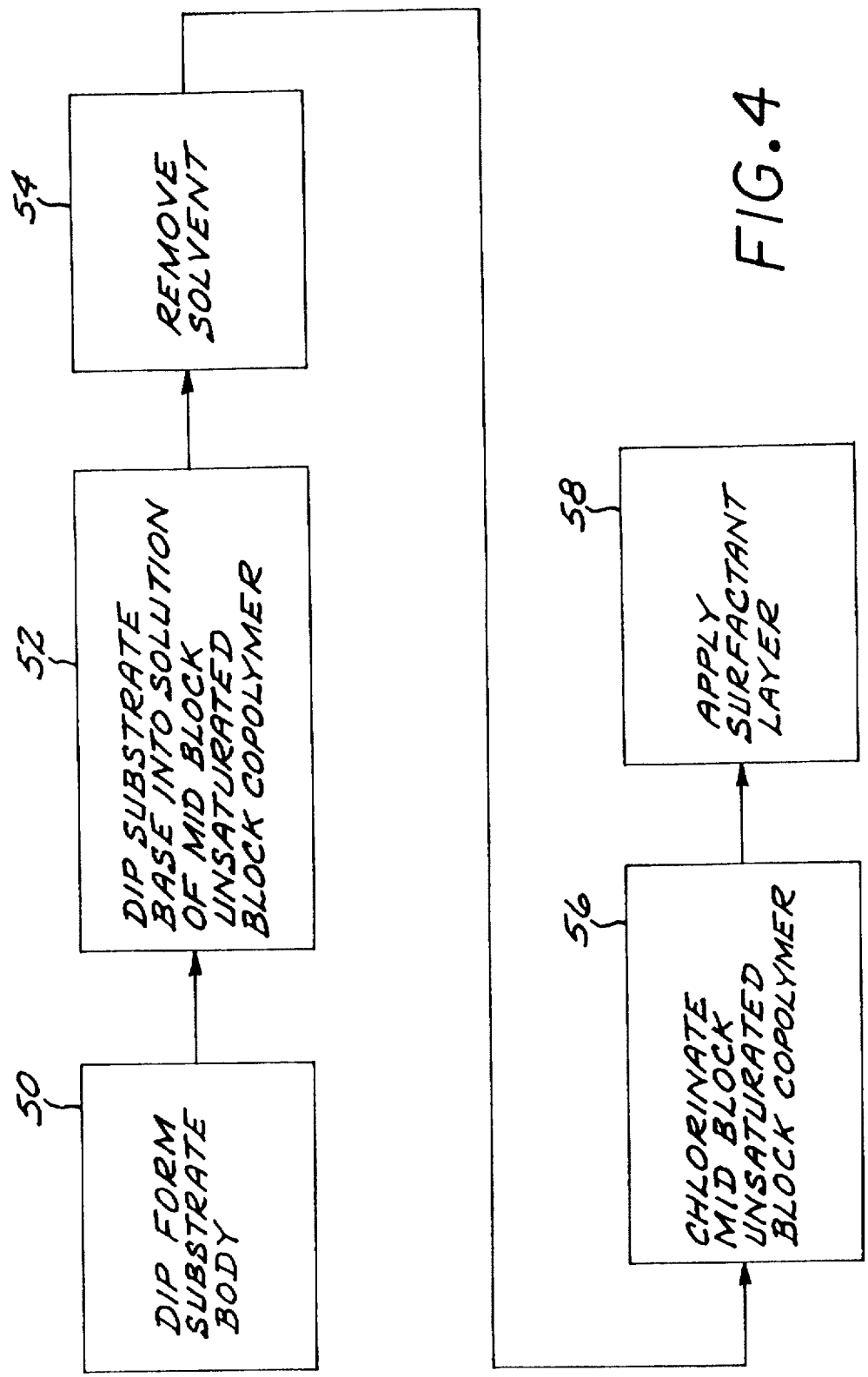

1

READILY DONNED, POWDER FREE ELASTOMERIC ARTICLE

BACKGROUND OF THE INVENTION

This invention relates to elastomeric articles such as gloves, and, more particularly, to such elastomeric articles specially treated to make them easy to slip on.

Highly elastic articles such as surgical and examination gloves have traditionally been made of natural latex in order to utilize its combination of good elasticity and strength. However, some persons are allergic to natural latex, and in addition natural latex is susceptible to environmental damage such as ozonation. For many years, the only available alternatives to natural latex were synthetic elastomers which did not produce allergic reactions, but which also tended to exhibit insufficient elasticity and strength, as well as susceptibility to ozone degradation in some cases.

An important advance in this area is the development of medical gloves made of S-EB-S (styrene-ethylene-butylene-styrene) synthetic elastomer block copolymers, as disclosed in U.S. Pat. Nos. 5,112,900 and 5,407,715. Articles such as gloves are readily dip-formed from such block copolymers, without the occurrence of pinholes that can result from impurities found in natural latex. The articles have substantially the same elastic and strength properties as natural rubber, are hypoallergenic, and are not subject to ozonation damage. Gloves made of S-EB-S block copolymers are available commercially from Tactyl Technologies, Inc., Vista, Calif.

Tightly fitting elastomeric articles, whether made of natural or synthetic elastomers, can be difficult to don. The elastomer action of the material of construction, its friction with the skin of the user, and the perspiration on the body of the user act in combination to make it difficult to slip the article on. To overcome this problem, it has been conventional practice to apply a powdered lubricant to the surface that is to contact the body of the user, such as the inside of the glove. As an example, epichloro-hydrin treated maize crosslinked starch is a common powder applied to the inside of elastomeric gloves during manufacture, to permit them to be more readily slipped onto the hand of the user.

The use of a powdered lubricant on the elastomer is operable, but has drawbacks in specific situations such as the case of surgical gloves. If some of the powder escapes from the inside of the glove into the surgical environment, as for example if the glove is torn during the surgery, the powder may enter the surgical wound to cause further complications for the patient. The powder may carry infectious agents, or the patient may be allergic to the powder.

Various other techniques are known for use with surgical gloves to improve their donning characteristics. These techniques include, for example, manufacturing the glove from a modified latex, using an inner layer of a hydrophilic polymer, applying a slip coating to the inner surface of the glove, providing lubricating particles on the inner surface of the glove, and other approaches.

While these techniques for producing powder-free gloves are perhaps operable in their conventional applications, the present inventors have found that they are not fully satisfactory for use with gloves made of the synthetic S-EB-S block copolymers and some other materials of construction. There is, accordingly, a need for an improved approach for providing a powder-free article such as a glove with acceptable donning characteristics. The present invention fulfills this need, and further provides related advantages.

SUMMARY OF THE INVENTION

The present invention provides an elastomeric, powder-free article having excellent donning characteristics. The article is preferably made using a substrate of synthetic elastomer that exhibits good elasticity and strength, is hypoallergenic, is resistant to environmental degradation, is producible by dip forming, and is otherwise acceptable for use. These properties are not adversely affected by the treatment and structure that provide improved donning characteristics, both initially and after aging of the article. The treatment for improving the donning characteristics is fully compatible with the forming of the underlying substrate. The approach of the invention is operable with a wide variety of substrate materials including, but not limited to, those made of S-EB-S block co-polymers such as those disclosed in U.S. Pat. Nos. 5,112,900 and 5,407,715.

In accordance with the invention, an elastomeric article comprises a substrate body made of an elastomeric material, preferably a mid block saturated styrene block copolymer such as an styrene-ethylene-butylene-styrene block copolymer, and a donning layer overlying at least one side of the substrate body. The donning layer comprises a chlorinated mid block unsaturated block copolymer such as a chlorinated styrene diene block copolymer, preferably chlorinated styrene-isoprene block copolymer. The styrene-isoprene block copolymer preferably has a polystyrene block content of from about 10 to about 20 percent by weight of the total copolymer weight and an end block polystyrene molecular weight of at least about 5,000 grams per mole. Optionally, a surfactant-containing layer may be applied overlying the donning layer.

The elastomeric article is manufactured by preparing the substrate body made of an elastomeric material by any operable technique, most preferably dip forming. The donning layer is applied to the substrate body by any operable technique, most preferably by dipping the substrate body into a solution of the mid block unsaturated block copolymer and thereafter chlorinating the mid block unsaturated block copolymer.

The elastomeric article of the invention has excellent elastic and strength properties, is hypoallergenic, is resistant to environmental degradation such as ozonation, is readily manufactured, and can be donned easily without the presence of any powder. The donning layer does not crack or peel from the substrate body during storage or service. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 4 is a block flow diagram for a preferred method of practicing the invention.

DETAILED DESCRIPTION OF THE INVENTION

Figure 1:
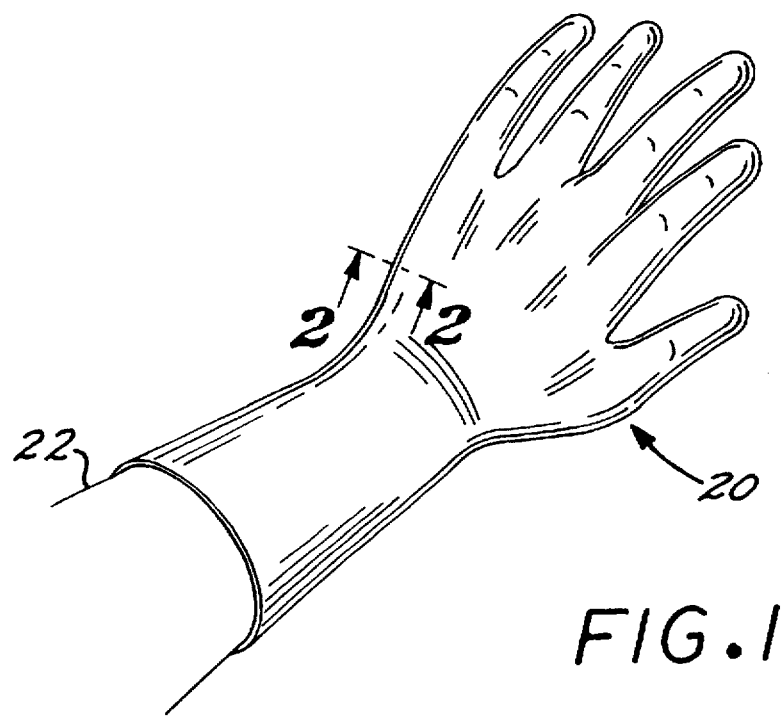
FIG. 1 is a perspective view of an elastomeric article made according to the invention.
Figure 2A:
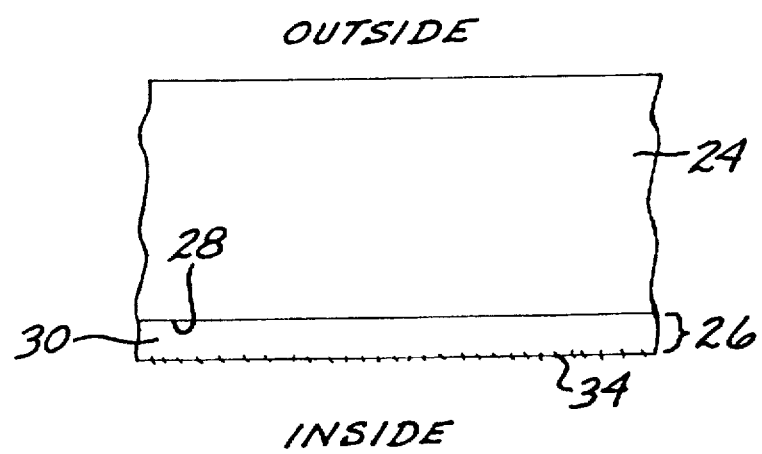
FIG. 2A is a sectional view through a first embodiment of the article of FIG. 1, taken generally along line 2—2.
Figure 2B:
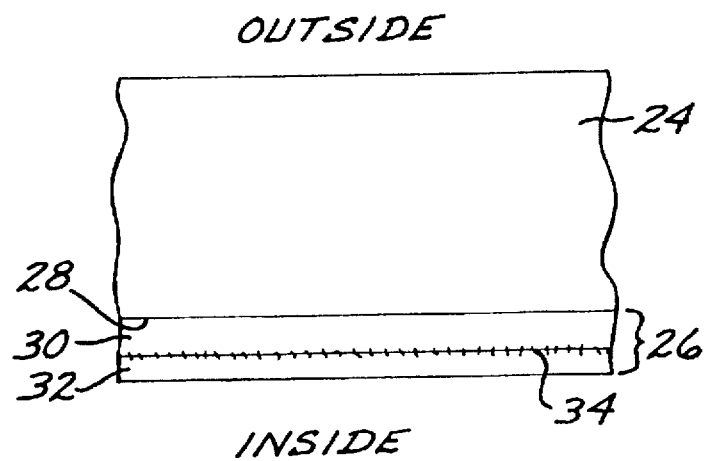
FIG. 2B is a sectional view through a second embodiment of the article of FIG. 1, taken generally along line 2—2.

FIG. 1 depicts an article made in accordance with the invention, in the preferred case a glove 20 on the hand of a user 22. FIGS. 2A and 2B illustrate the structure of two preferred embodiments of the glove 20. In both embodiments, the glove includes a substrate body 24 having the basic shape of the article, and a coating 26 on an inside surface 28 of the substrate body 24 that is to contact the body of the user 22 during service. The coating 26 includes a donning layer 30 overlying, contacting, and bonded to the substrate body 24. The embodiment of FIG. 2B further includes a surfactant layer 32 overlying and contacting the donning layer. FIGS. 2A and 2B are presented to illustrate the positions of the elements, and are not drawn to scale. The surfactant layer 32, for example, is typically at most only a few molecules thick.

The substrate body 24 is made of an elastomeric material, desirably comprising at least one styrene-ethylene-butylene-styrene (S-EB-S) block copolymer, and preferably a mixture of S-EB-S block copolymers. Most preferably, the elastomeric material of the substrate body 24 includes a block copolymer component comprising at least two, and most preferably three, S-EB-S block copolymers. Each block copolymer has from about 25 to about 35 percent by weight of polystyrene blocks. The total mass of S-EB-S block copolymers has from about 40 to about 60 percent by weight of a first S-EB-S block copolymer with a solution viscosity of about 6500 cps at 25 percent by weight of copolymer in toluene at 77° F., from about 15 to about 59 percent by weight of a second S-EB-S block copolymer with a solution viscosity of about 2000 cps in toluene at 10 percent weight of polymer in toluene at 77° F., and from about 1 to about 40 percent by weight of a third S-EB-S block copolymer having a solution viscosity of about 1600 cps in toluene at 25 percent weight of polymer in toluene at 77° F. The most preferred elastomeric material further includes a plasticizer in an amount of from about 30 to about 65 parts by weight of the total mass of the S-EB-S block copolymer component. The article is fabricated by dipping a form into a liquid solution of the elastomer a sufficient number of times to build up the desired thickness on the form. This elastomeric material and the fabrication process are described more fully in U.S. Pat. Nos. 5,112,900 and 5,407,715, whose disclosures are incorporated by reference.

Figure 3:
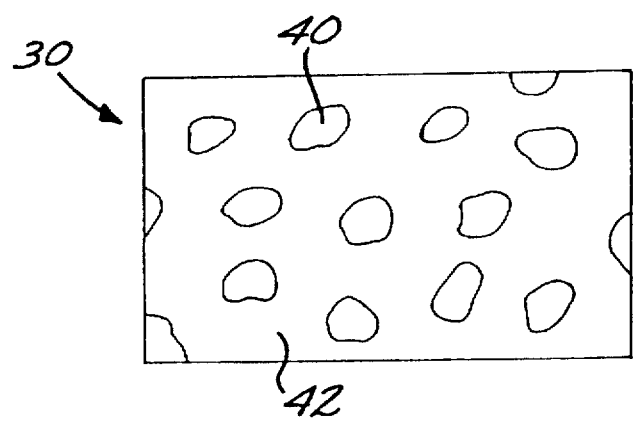
FIG. 3 is a schematic illustration of the microstructure of the styrene-isoprene-styrene material.

The donning layer 30 comprises a chlorinated mid block unsaturated styrene-isoprene (SIS) block copolymer. The SIS block copolymer may include tri- or radial-blocks. The SIS block copolymer preferably has a polystyrene end block content of from about 10 to about 20 percent by weight, most preferably from about 15 to about 18 percent by weight, of the total weight of the SIS block copolymer. If the polystyrene end block content is below about 10 percent by weight, optimum strength properties are not achieved at higher temperatures. If the polystyrene end block content is above about 20 percent by weight, the treated surface of the article tends to be too smooth, promoting blocking and glare of the article, and also tends to stiffen the final article. Too high a polystyrene end block content is particularly to be avoided when the donning layer is used on a dip-formed substrate body. A further reason for selecting a maximum polystyrene end block content of about 20 percent by weight of the total SIS block copolymer is that this content produces a morphology of polystyrene domains 40 dispersed in a continuous polyisoprene matrix 42 in the donning layer 30, as illustrated in FIG. 3. This morphology results in good bonding of the donning layer 30 to the substrate body 24, both initially and after aging, and also imparts good elasticity to the donning layer so that it can stretch with the elastomer of the substrate body 24 without cracking. The donning layer also has good crack and peel resistance as a result of its composition and morphology. Polystyrene block contents greater than about 20 percent by weight result in a more agglomerated structure.

The molecular weight of the polystyrene end blocks is preferably at least about 5,000 grams per mole. It has been found that SIS block copolymers having polystyrene end blocks of molecular weight less than about 5,000 grams per mole have increased adhesion and blocking tendency, both initially and after heat aging. Blocking is the adhesion or sticking together of adjacent articles and, where present, causes the gloves to be difficult to open for insertion of the hand and also causes neighboring gloves to stick together in a package. A polystyrene end block molecular weight of more than about 5,000 grams per mole has been found to reduce this undesirable blocking, particularly when the substrate body is formed by a dip-forming technique.

Examples of suitable mid-block unsaturated SIS block copolymers include Kraton® D1107 available from Shell Chemical Co. and Vector® 511 and Vector® 4111 available from Dexco. The Vector® 4111 product, for example, contains 17.5–19.0 percent by weight styrene end blocks.

The material of the donning layer 30 can also be made of other polymers having reactive sites which can react with chlorine in the subsequent chlorination procedure. Elastomers having no such sites reactive with chlorine are not operable.

The donning layer 30 of mid block unsaturated SIS block copolymer has a chlorinated surface remote from the surface 28, indicated schematically at numeral 34 in FIGS. 2A and 2B. The chlorine atoms react with the mid-block (unsaturated) polyisoprene, modifying the tackiness of the layer slightly. Other halogens such as bromine or iodine could also be used, but are less preferred.

The surfactant layer 32 overlies the donning layer 30 in the embodiment of FIG. 2B. The surfactant layer 32 aids in donning the article when the user's body is either wet or dry and also reduces the tendency to blocking. The surfactant layer preferably comprises a cationic, an anionic, or a nonionic surfactant. Most preferably, the surfactant layer 32 is cetyl pyridinium chloride or sodium lauryl sulfate, optionally mixed with a medical-grade silicone such as Dow Corning 365 silicone.

By way of example, the substrate body 24 in the case of a glove produced by dip forming is preferably from about 0.004 to about 0.012 inches thick. The donning layer 30 cannot be readily expressed as having a thickness, but about 0.15 grams of the mid block unsaturated styrene-isoprene (SIS) block copolymer is used per glove. The chlorinated region 34 and the surfactant layer 32, where present, are more in the nature of surface treatments. These values are provided by way of illustration and not limitation.

FIG. 4 illustrates the preferred approach for practicing the invention. The substrate body is prepared, preferably by dip forming, numeral 50. The preferred dip forming technique is discussed fully in U.S. Pat. Nos. 5,112,900 and 5,407,715. Briefly, the S-EB-S block copolymers are mixed with a plasticizer. The plasticizer is preferably a mineral oil, which is a refined petroleum paraffinic hydrocarbon oil. The preferred mineral oil has a specific gravity of 0.87 at 77° F., a viscosity of 170 centistokes at 77° F., and a Hirschler molecular weight of 492. The S-EB-S block copolymers are furnished by the manufacturer as a solid. To form a solution from which articles can be dip formed, the S-EB-S block copolymers and the mineral oil plasticizer are dissolved in a mutual solvent, preferably toluene. Toluene solutions of S-EB-S provide minimal viscosities of concentrated solutions compared to many other solvents. A highly concentrated solution improves dip-forming process economics by reducing the amount of solvent that must be processed in a solvent recovery operation. The S-EB-S in toluene solution is a true, stable solution, as distinct from a mixture or an emulsion. The process requires attaining such a solution, as by using a high shear mixer and mixing for a sufficient time to reach a homogeneous solution. The solution is filtered to remove any fine particulate matter.

To prepare the glove by dip forming, a sufficiently large amount of the S-EB-S elastomer solution is prepared in the manner described and placed into a dipping tank, at ambient temperature. A commercially available form (typically made of aluminum, glass, plastic, or porcelain) in the shape of the desired article is dipped into the tank and removed slowly, leaving a thin, uniform layer of the liquid elastomer solution deposited onto the form, much in the same manner that a layer of paint would be deposited upon the form if it were dipped into a container of paint. The form is dried in a stream of air for a predetermined time to permit the solvent in the thin elastomeric layer to evaporate, at ambient temperature. The dipping procedure is repeated as necessary to build up a substrate body of the required thickness.

The substrate body is dipped into a solution of the mid block unsaturated block copolymer to deposit the block copolymer onto the surface of the substrate body, numeral 52. The preferred SIS mid block unsaturated block copolymer is dissolved into a solvent such as toluene in a dilute concentration, preferably about 4 percent by weight. In practice, the outside of the article is coated, and later turned inside out.

The solvent in which the SIS block copolymer is dissolved is removed, numeral 54, preferably by air drying.

The layer of mid block unsaturated block copolymer is chlorinated, numeral 56. Any operable chlorinating approach may be used. A number of operable techniques utilized by the inventors are described in the subsequent examples. The most preferred chlorination procedure is that discussed below in Example 8.

Optionally, the surfactant layer is applied overlying the donning layer, numeral 58. When this option is used, a 0.5 percent aqueous solution of cetyl pyridinium chloride or sodium lauryl sulfate is prepared, and the surface of the article having the donning layer is contacted to the solution for about 15 seconds at ambient temperature.

The following examples illustrate the practice of the invention, but should not be interpreted as limiting the invention in any respect. For all of these examples, the substrate body is an S-EB-S dip-formed glove prepared according to the approach described above and in U.S. Pat. Nos. 5,112,900 and 5,407,715. These studies were performed to validate the powder-free donning approach of the invention, and there was no attempt to optimize the performance of the gloves or to meet commercial standards.

EXAMPLE 1

While still on the former but after drying, the glove was dipped into a 4 percent by weight solution of Vector® 511 SIS block copolymer in toluene. The SIS solution on the glove was air dried to remove the solvent. The glove was dipped into a solution of 4905 grams of water, 70 grams of sodium hypochlorite (14 percent by weight in water), and sufficient hydrochloric acid to produce a solution having a pH of 2, for a period of about 15 minutes, and dried. The glove was then stripped from the former. It showed good dry donning characteristics without the use of any powder.

EXAMPLE 2

Example 1 was repeated, except that the chlorinating solution contained 4050 grams of water, 700 grams of sodium hypochlorite, and 250 grams of hydrochloric acid, and the immersion time was 1 minute. After drying and removing from the form, the glove showed good dry donning characteristics without the use of any powder.

EXAMPLE 3

Example 1 was repeated, except that the chlorinating solution contained 4953 grams of water, 35 grams of sodium hypochlorite, and 12.5 grams of hydrochloric acid, and the immersion time was 20 minutes. After drying and removing from the form, the glove showed a tendency to block due to the low level of chlorination.

EXAMPLE 4

Example 1 was repeated for a batch of 20 gloves, for the dip forming and SIS coating steps (but not for the chlorinating step, which was accomplished by a different approach as described subsequently). Before stripping the gloves from their forms, dry cornstarch powder was applied. The powdered gloves were loaded into a washing machine with 11.4 grams of Surfynol TG® surfactant mixed into 38 liters of water. The gloves were run in the washing machine for 15 minutes at low agitation and removed from the washer. The washer was then filled with a solution of 38 liters of clean water, 1994 grams of 7 percent chlorox® bleach (2300 ppm chlorine), and 460 milliliters of 6N sulfuric acid, the solution having a pH of 2.2 at 18.9° C. The wet gloves were added with the SIS coating on the outside of the gloves and agitated for 15 minutes. The measured pH of the solution rose to 2.41 in 5 minutes, 2.64 after 10 minutes, and 2.68 after 15 minutes. After 15 minutes, the solution was neutralized with 180 milliliters of 3N potassium hydroxide to a pH of 7.02, and the gloves were further agitated for 15 minutes and removed. The gloves were rinsed with fresh cold water with 5 minutes of agitation, rinsed again with fresh cold water for 5 minutes of agitation. The gloves were removed from the washing machine, dried on low for 40 minutes, inverted, and dried on low for another 10 minutes. The powder-free gloves produced showed good dry donning characteristics with a slight yellowish color.

EXAMPLE 5

Example 4 was repeated, except that the SIS-containing Vector® 511 SIS block copolymer solution was 3 percent by weight rather than 4 percent by weight as in Example 4. The finished gloves were gamma sterilized in their packages at 2.5 Mrad dose. Control specimens with the powder coating were retained, and some of these specimens were also packaged and gamma sterilized. Samples of powder-coated and SIS-coated and chlorinated gloves were aged at 70° C. for 166 hours. Specimens for mechanical testing were retained at the various stages. Mechanical testing was performed, with the following results:

| Specimen | 500% Modulus (MPa) | Tensile Strength (MPa) | Elongation (%) |
|---|---|---|---|
| Example 5 sterilized | 3.14 | 23.36 | 942 |
| Example 5 sterilized + aged | 3.20 | 21.94 | 934 |
| Powdered and sterilized | 3.05 | 25.22 | 959 |
| Powdered and sterilized + aged | 3.6 | 28.19 | 913 |

EXAMPLE 6

A batch of 8 pairs of gloves were prepared in the manner described in Example 4, for the dip forming and SIS coating steps (but not for the chlorinating step, which was accomplished by a different approach as described subsequently). Before stripping the gloves from their forms, precipitate calcium carbonate powder was applied to prevent sticking. The stripped gloves were placed into a washing machine containing a pH 2.03 solution of 38 liters of water, 1994 grams of sodium hypochlorite, and 710 milliliters of 6N sulfuric acid. The gloves were agitated in the solution for 15 minutes, during which time the pH rose from 2.03 to 2.26.

The solution was then neutralized with 450 milliliters of 3N potassium hydroxide to a pH of 7.05. The water solution was drained and the gloves spun in the washer for 3 minutes, rinsed twice with water for 3 minutes each, and dried in a drying on low setting for 40 minutes. The gloves were inverted and dried for an additional 15 minutes. The gloves had a light yellow color and showed good dry donning characteristics without the application of powder. The samples showed very little blocking on the S-EB-S (substrate body) side, and no blocking on the chlorinated SIS (donning layer) side after heat aging at 60° C. for 14 hours in the package, under a weight of 50 pairs of gloves.

EXAMPLE 7

A batch of 64 pairs of gloves were prepared in the manner described in Example 6, for the dip forming and SIS coating steps (but not for the chlorinating step, which was accomplished by a different approach as described subsequently). The stripped gloves were placed into a washing machine containing a pH 2.01 solution of 38 liters of water, 2294 grams of sodium hypochlorite, and 650 milliliters of 6N sulfuric acid. After the gloves were added, the pH rose to 2.31, and sufficient 6N sulfuric acid was added to bring the pH to 2.28. The gloves were agitated in the solution for 15 minutes. The solution was then neutralized with 500 milliliters of 3N potassium hydroxide to a pH of 7.55. The water solution was drained and the gloves spun in the washer for 3 minutes and rinsed twice with water for 15 minutes each.

Twenty-five pairs of the gloves were thereafter dried at 130° F. for 40 minutes, inverted, and dried for another 20 minutes. The gloves showed good dry donning characteristics and fair wet/damp donning characteristics.

Fourteen pairs of the gloves were rinsed in an aqueous solution of 0.25 weight percent cetyl pyridinium chloride and 0.05 weight percent Dow Corning silicone emulsion DC365, and dried at 130° F. for 40 minutes, inverted, and dried for another 20 minutes. The gloves had wet/damp donning characteristics superior to the samples that were untreated with the cetyl pyridinium chloride/silicone emulsion solution.

Twenty-five pairs of the gloves were rinsed in an aqueous solution of 0.5 weight percent cetyl pyridinium chloride and 0.1 weight percent Dow Corning silicone emulsion DC365, and dried at 130° F. for 40 minutes, inverted, and dried for another 20 minutes. These gloves had good dry donning characteristics, and improved wet donning characteristics compared to the gloves of the other two groups of this Example 7. However, there was a sensation of a slight soapy residue in the interior of the gloves.

All samples showed reduced blocking tendencies on the S-EB-S (substrate body) side after 60° C. aging in the package under a weight of 50 pairs of gloves, with the improvement greatest for the gloves treated with the cetyl pyridinium chloride/silicone emulsion solution.

EXAMPLE 8

A batch of 63 pairs of gloves were prepared in the manner described in Example 4, for the dip forming step (but not for the SIS-treatment or chlorinating steps, which were accomplished by a different approach as described subsequently). The SIS treatment was performed as in Example 4, except that the solution was 4 percent by weight of Vector® 4111® block copolymer in toluene. The samples were dusted with precipitated calcium carbonate before stripping them from the formers. The gloves were chlorinated by loading them into a washing machine having a pH 2.01 solution of 38 liters of water, 2294 grams of Chlorox bleach, and 650 milliliters of 6N sulfuric acid. After the gloves were loaded and subjected to mild agitation, the pH rose to 2.31. An additional 75 grams of sulfuric acid was added to reduce the pH to 2.28. The gloves were agitated for 15 minutes, the solution was neutralized to pH 7.15 by adding 500 milliliters of 3N potassium hydroxide, the solution was drained, and the gloves were rinsed with water twice for 15 minutes each time.

One set of 21 pairs of gloves, termed group 8-1, were dried at 130° F. for 40 minutes, inverted, and dried for another 20 minutes.

A second set of 21 pairs of gloves, termed group 8-2, were coated on their insides with a solution of 1984 grams of water, 10 grams of cetyl pyridinium chloride, and 5.7 grams of Dow Corning silicone DC365 and dried as for the group 8-1 gloves.

A third set of 21 pairs of gloves, termed group 8-3, were rinsed with a solution of 666.7 grams of the solution prepared for the group 8-2 gloves diluted with 666.7 grams of water, and dried as for the group 8-1 gloves.

All three groups exhibited good dry donning characteristics, and the gloves of groups 8-2 and 8-3 showed good dry, wet, and damp donning characteristics.

The gloves of group 8-1, after sterilization, showed a tensile strength of 23.39 MPa and an elongation at break of 865%. The samples did not show any significant change in properties after heat aging at 70° C. for 166 hours.

The gloves of group 8-3 after aging for 20 minutes in an ozone chamber at about 250 ppm (parts per million) of ozone showed a tensile strength of 27.79 MPa and an elongation at break of 881%.

All samples showed a residue of less than 2 milligrams per glove when the residue was determined by rinsing the gloves with 150 milliliters of de-ionized water and determining the dried residue after filtration using a 3 micron nitrocellulose filter.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An elastomeric article, comprising:
   a substrate body made of an elastomeric material; and
   a donning layer overlying at least one side of the substrate body, the donning layer comprising a chlorinated mid block unsaturated block copolymer.

2. The elastomeric article of claim 1, wherein the substrate body has the form of a glove having an inside surface, and the donning layer over lies the inside surface of the glove.

3. The elastomeric article of claim 1, wherein the elastomeric material of the substrate body comprises a mid block saturated styrene block copolymer.

4. The elastomeric article of claim 1, wherein the elastomeric material of the substrate body comprises an styrene-ethylene-butylene-styrene block copolymer.

5. The elastomeric article of claim 1, wherein the chlorinated mid block unsaturated block copolymer is a chlorinated styrene-isoprene block copolymer.

6. The elastomeric article of claim 1, wherein the chlorinated mid block unsaturated block copolymer is chlorinated styrene-isoprene block copolymer having a polystyrene block content of from about 10 to about 20 percent by weight of the total copolymer weight.

7. The elastomeric article of claim 1, wherein the chlorinated mid block unsaturated block copolymer is chlorinated styrene-isoprene-styrene having an end block polystyrene molecular weight of at least about 5,000 grams per mole.

8. The elastomeric article of claim 1, wherein the chlorinated mid block unsaturated block copolymer is chlorinated styrene-isoprene having a morphology of polystyrene domains dispersed in a continuous polyisoprene matrix.

9. The elastomeric article of claim 1, further including a surfactant layer overlying the donning layer.

10. The elastomeric article of claim 1, further including a surfactant layer overlying the donning layer, the surfactant layer comprising a surfactant selected from the group consisting of cetyl pyridinium chloride and sodium lauryl sulfate.

11. An elastomeric article, comprising:

a glove body made of an styrene-ethylene-butylene-styrene block copolymer; and a donning layer overlying at least one side of the substrate body, the donning layer comprising a chlorinated mid block unsaturated styrene-isoprene block copolymer having a polystyrene block content of from about 10 to about 20 percent by weight of the total copolymer weight and wherein the end block polystyrene molecular weight is at least about 5,000.

12. A method for preparing an elastomeric article, comprising the steps of:

preparing a substrate body made of an elastomeric material; and applying a donning layer overlying at least one side of the substrate body, the donning layer comprising a chlorinated mid block unsaturated block copolymer.

13. The method of claim 12, wherein the step of preparing includes the step of preparing the substrate body in the shape of a glove.

14. The method of claim 12, wherein the step of preparing includes the step of dip forming the elastomeric material into the shape of a glove.

15. The method of claim 12, wherein the step of preparing includes the step of providing an elastomeric material comprising an styrene-ethylene-butylene-styrene block copolymer.

16. The method of claim 12, wherein the step of applying includes the step of providing a solution of mid block unsaturated styrene-isoprene block copolymer in a solvent;

contacting the solution of mid block unsaturated styrene-isoprene block copolymer in a solvent to at least one side of the substrate body; and removing the solvent to leave a solid layer of unsaturated styrene-isoprene on the surface of the substrate body.

17. The method of claim 16, including an additional step, after the step of removing, of contacting the solid layer of mid block unsaturated styrene-isoprene with a source of chlorine.

18. The method of claim 17, wherein the step of contacting the layer includes a step of contacting the layer with a source of chlorine selected from the group consisting of a solution of chlorine dissolved in water and a solution of sodium hypochlorite bleach and a dilute acid.

19. The method of claim 12, wherein the step of preparing a substrate body includes the steps of providing an elastomeric material comprising an styrene-ethylene-butylene-styrene block copolymer; and dip forming the elastomeric material into the shape of a glove; wherein the step of applying includes the steps of providing a solution of mid block unsaturated styrene-isoprene block copolymer in a solvent, contacting the solution of mid block unsaturated styrene-isoprene block copolymer in a solvent to at least one side of the substrate body, and removing the solvent to leave a solid layer of unsaturated styrene-isoprene on the surface of the substrate body;

further including an additional step, after the step of applying a donning layer, of contacting the solid layer of mid block unsaturated styrene-isoprene with a source of chlorine; and further including an additional step, after the step of contacting the solid layer, of contacting the chlorinated solid layer with a surfactant selected from the group consisting of cetyl pyridinium chloride and sodium lauryl sulfate.

20. The article of claim 11, wherein the chlorinated mid block unsaturated styrene-isoprene block copolymer has a morphology of polystyrene domains dispersed in a continuous polyisoprene matrix.

* * * * *